US012800486B2

(12) United States Patent
Al Ibrahim et al.

(10) Patent No.: US 12,800,486 B2
(45) Date of Patent: Nov. 17, 2026

(54) SELF-CALIBRATING THREE-PHASE FLOW WATER-CUT LASER SENSING USING AN UNSUPERVISED MACHINE LEARNING MODEL

(71) Applicants: King Abdullah University of Science and Technology, Thuwal-Jeddah (SA); SAUDI ARABIAN OIL COMPANY, Dhahran (SA)

(72) Inventors: Emad Al Ibrahim, Thuwal-Jeddah (SA); Muhammad Arsalan, Dhahran (SA); Aamir Farooq, Thuwal-Jeddah (SA)

(73) Assignees: SAUDI ARABIAN OIL COMPANY, Dhahran (SA); KING ABDULLAH UNIVERSITY OF SCIENCE AND TECHNOLOGY, Thuwal-Jeddah (SA)

( * ) Notice: Subject to any disclaimer, the term of this patent is extended or adjusted under 35 U.S.C. 154(b) by 366 days.

(21) Appl. No.: 18/656,432

(22) Filed: May 6, 2024

(65) Prior Publication Data

US 2025/0341463 A1 Nov. 6, 2025

(51) Int. Cl.

*G01N 21/3577* (2014.01)
*G01N 33/28* (2006.01)
*G06N 3/084* (2023.01)

(52) U.S. Cl.

CPC ..... *G01N 21/3577* (2013.01); *G01N 33/2823* (2013.01); *G01N 33/2847* (2013.01); *G06N 3/084* (2013.01); *G01N 2201/12723* (2013.01)

(58) Field of Classification Search

CPC ........... G01N 21/3577; G01N 33/2823; G01N 33/2847; G01N 2201/12723; G06N 3/084
See application file for complete search history.

(56) References Cited

U.S. PATENT DOCUMENTS 5,576,974 A 11/1996 Marrelli et al.
6,076,049 A 6/2000 Lievois et al.
(Continued)

FOREIGN PATENT DOCUMENTS

WO 2023229821 A1 11/2023

OTHER PUBLICATIONS

International Search Report issued in corresponding International Application No. PCT/US2025/027698; mailed Aug. 12, 2025 (5 pages).

(Continued)

*Primary Examiner* — Yoshihisa Ishizuka
(74) *Attorney, Agent, or Firm* — Osha Bergman Watanabe & Burton LLP

(57) ABSTRACT

Systems and methods for a self-calibrating three-phase flow water-cut laser sensing using an unsupervised machine learning model are disclosed. The methods include creating a training data set, wherein the training data set comprises training mixture spectra; training, using the training data set, an unsupervised machine learning model to estimate an estimated water-cut and an estimated path-length fraction value, wherein, via the training, the unsupervised machine learning model calibrates itself to determine the estimated water-cut and the estimated path-length fraction value; obtaining an observed mixture spectrum from a water-cut laser sensor; estimating, using the trained unsupervised machine learning model, the estimated water-cut and the estimated path-length fraction value from the observed mixture spectrum; determining, from the estimated path-length fraction value, an estimated gas fraction value; and determining a composition of fluids in a separator using the estimated water-cut and the estimated gas fraction value.

20 Claims, 10 Drawing Sheets

(56) References Cited

U.S. PATENT DOCUMENTS

| | | | | |
|---|---|---|---|---|
| 2010/0274503 | A1 | 10/2010 | Hurmuzlu et al. | |
| 2015/0300273 | A1* | 10/2015 | Hunter | F02D 41/0027 250/343 |
| 2021/0102831 | A1 | 4/2021 | Ahmad et al. | |
| 2023/0400398 | A1 | 12/2023 | Mcfarlane et al. | |

OTHER PUBLICATIONS

Written Opinion of the International Searching Authority issued in corresponding International Application No. PCT/US2025/027698; dated Aug. 12, 2025 (7 pages).

* cited by examiner

SELF-CALIBRATING THREE-PHASE FLOW WATER-CUT LASER SENSING USING AN UNSUPERVISED MACHINE LEARNING MODEL

A water-cut laser sensor may be used to determine the water-cut in a fluid mixture. However, existing laser sensors require calibration to correctly identify species (i.e., components of the mixture) and avoid sensor drift over time. Furthermore, current methods can only be applied to two-phase flows (water and oil).

Existing calibration-free methods remove outliers from recorded measurements and use regression techniques to determine the water-cut. While this works for two-phase flows, it does not generalize to three-phase flows (oil-water-gas mixtures) where the path length of a laser beam is variable.

Machine learning models may outperform regression methods, but typically use supervised learning schemes which require a large quantity of labeled data, that may be difficult, time-consuming, and costly to obtain. Therefore, there exists a pressing need for an unsupervised machine learning model that produces accurate results for three-phase flows and can determine water-cut and path-length fraction values without labeling data in a supervised fashion.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments disclosed herein relate to methods for a self-calibrating three-phase flow water-cut laser sensing using an unsupervised machine learning model are disclosed. The methods include creating a training data set, wherein the training data set comprises training mixture spectra; training, using the training data set, an unsupervised machine learning model to estimate an estimated water-cut and an estimated path-length fraction value, wherein, via the training, the unsupervised machine learning model calibrates itself to determine the estimated water-cut and the estimated path-length fraction value; obtaining an observed mixture spectrum from a water-cut laser sensor; estimating, using the trained unsupervised machine learning model, the estimated water-cut and the estimated path-length fraction value from the observed mixture spectrum; determining, from the estimated path-length fraction value, an estimated gas fraction value; and determining a composition of fluids in a separator using the estimated water-cut and the estimated gas fraction value.

In general, in one aspect, embodiments disclosed herein relate to a system for a self-calibrating three-phase flow water-cut laser sensing using an unsupervised machine learning model are disclosed. The system includes a computer processor configured to: create a training data set, wherein the training data set comprises training mixture spectra; train, using the training data set, an unsupervised machine learning model to estimate an estimated water-cut and an estimated path-length fraction value, wherein, via the training, the unsupervised machine learning model calibrates itself to determine the estimated water-cut and the estimated path-length fraction value; obtain an observed mixture spectrum from a water-cut laser sensor; estimate, using the trained unsupervised machine learning model, the estimated water-cut and the estimated path-length fraction value from the observed mixture spectrum and determine a composition of fluids in a separator using the estimated water-cut and the estimated path-length fraction value; and determine, using the estimated path-length fraction value, an estimated gas fraction value.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

Figure 1A:
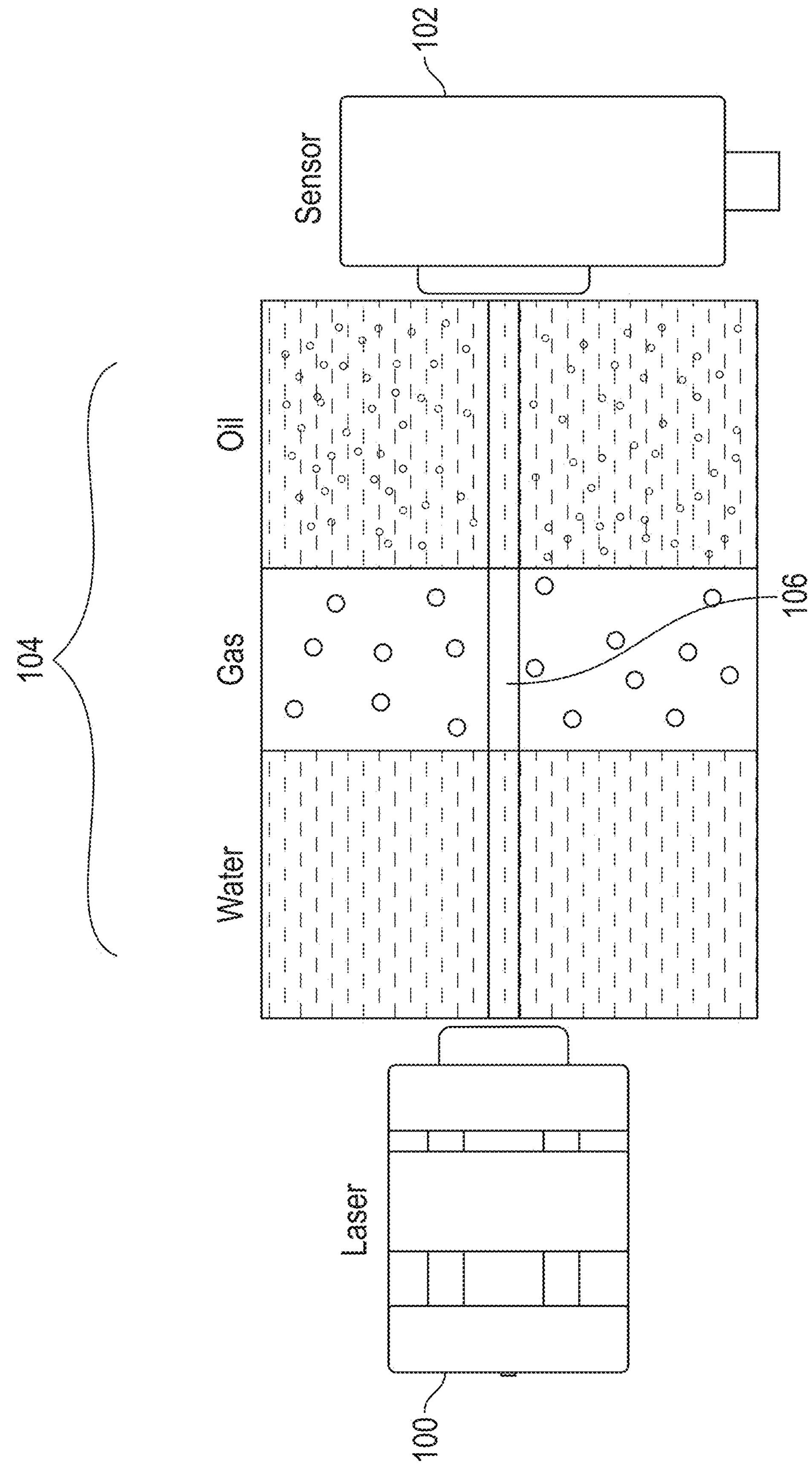
FIG. 1A shows a laser, a sensor, and a fluid mixture, in accordance with one or more embodiments.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

In the following description of FIGS. 1-6, any component described with regard to a figure, in various embodiments disclosed herein, may be equivalent to one or more like-named components described with regard to any other figure. For brevity, descriptions of these components will not be repeated with regard to each figure. Thus, each and every embodiment of the components of each figure is incorporated by reference and assumed to be optionally present within every other figure having one or more like-named components. Additionally, in accordance with various embodiments disclosed herein, any description of the components of a figure is to be interpreted as an optional embodiment which may be implemented in addition to, in conjunction with, or in place of the embodiments described with regard to a corresponding like-named component in any other figure.

It is to be understood that the singular forms "a," "an," and "the" include plural referents unless the context clearly dictates otherwise. Thus, for example, reference to "a self-calibrating model" includes reference to one or more of such self-calibrating models.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that one or more of the steps shown in the flowcharts may be omitted, repeated, and/or performed in a different order than the order shown. Accordingly, the scope disclosed herein should not be considered limited to the specific arrangement of steps shown in the flowcharts.

Although multiple dependent claims are not introduced, it would be apparent to one of ordinary skill that the subject matter of the dependent claims of one or more embodiments may be combined with other dependent claims.

A novel unsupervised machine learning model to self-calibrate a water-cut laser sensor is disclosed. The unsupervised machine learning model is used for self-calibration and may continually adapt to prevent sensor drift. The model may calibrate itself to determine the water-cut, WC, and the gas fraction, GF, using only field measurements without the need for prior calibration or knowing what oils are in the flow. Additionally, the model works with variable path-lengths of a laser through a medium, thus ensuring applicability to three-phase flows. "Calibration" and "self-calibration" in the context of this document may be understood as synonyms for training.

Water-cut is the ratio of water produced compared to the volume of total liquids produced in an oil reservoir. Estimating the water-cut is a key process in managing an oilfield. It may be used to calculate the amount of produced fluid that can eventually be sold. In addition, the water-cut values and/or the change in value over time may trigger or inform decisions to alter production parameters, including production flow rates, injection rates, shut-ins, and the drilling of additional wellbores.

A number of technologies have been developed to determine water-cut, including Coriolis densitometers, microwave analyzers, capacitance analysis, and infrared spectrometers. Infrared water-cut sensors typically rely on near-infrared absorption spectroscopy and are capable of measuring a full range (0 to 100%) water-cut. The technology is based on a difference between the absorption of infrared radiation by oil and water. It is well known to a person of ordinary skill in the art that there are peaks in the near-infrared frequency spectrum where water absorbs more energy than oil. In this way, a water-cut sensor based on spectroscopy exploits differences in absorption properties of oil and water.

FIG. 1A presents an illustrative example layout of a laser used to measure spectra from a mixture of water, gas, and oil. On the left side of FIG. 1A is the laser (100). On the right side of FIG. 1A is the sensor (102) that measures the received signal; various frequencies of the laser beam (106) traveling from the laser (100) to the sensor (102) may be absorbed to a greater or less extent depending on the composition of the fluid mixture (104). While the fluid mixture (104) is illustrated conceptually as species including water, gas, and oil. However, in reality, the spatial distribution of the species may have a complex heterogeneous form.

Figure 1B:
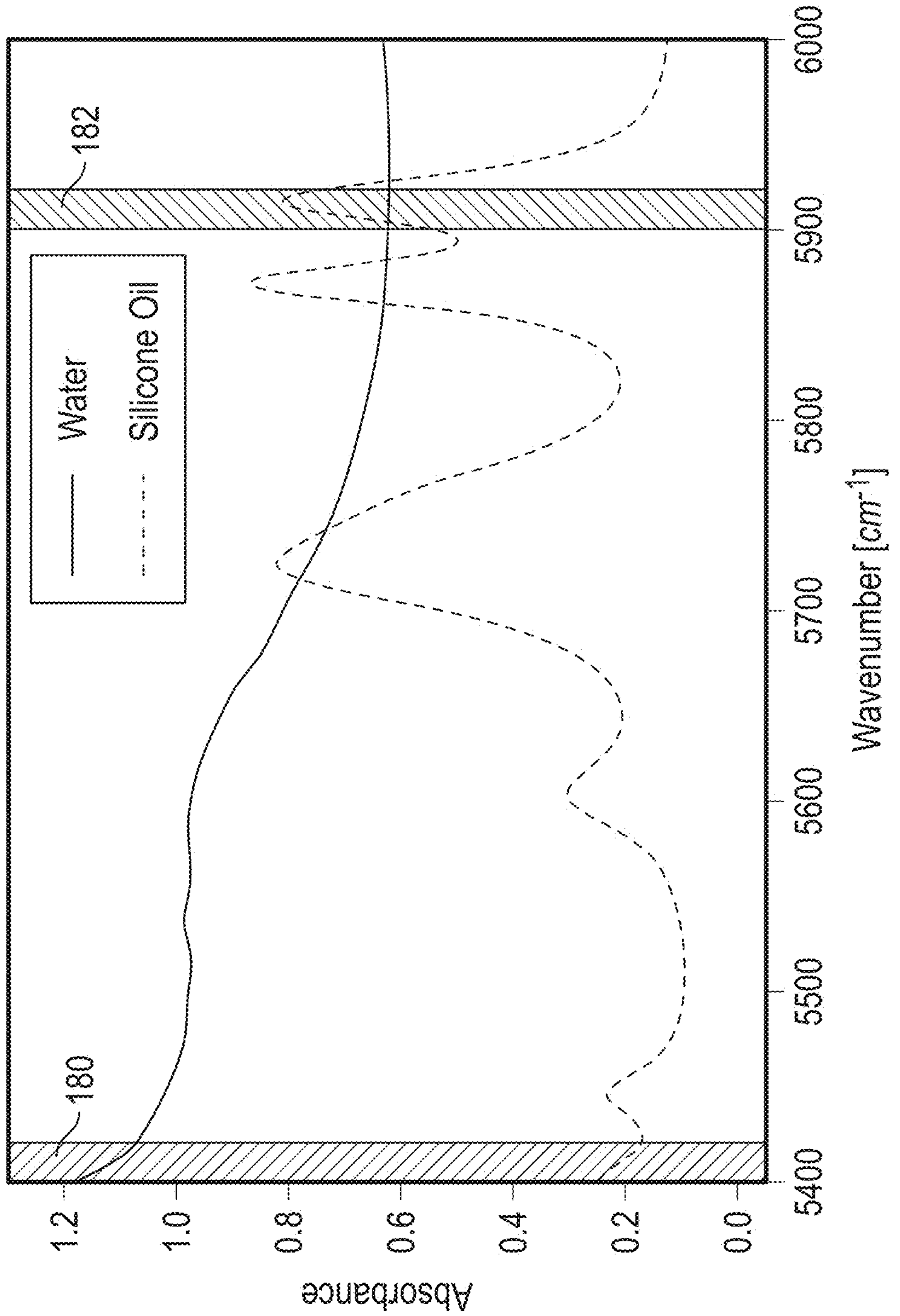
FIG. 1B shows an absorbance spectrum, in accordance with one or more embodiments.

Wavelength selection depends on finding relatively strong absorbing features for both water and oil. The 5400-6000 $cm^{-1}$ range shown in FIG. 1B is an example of a suitable range to operate the model, but the model is not limited to this range. Note that water absorbance dominates in the first shaded area (180) closer to 5400 $cm^{-1}$ while oil surrogates dominate near the second shaded area (182) close to 5900 $cm^{-1}$, which helps in the convergence of the calibration process.

Generally, probing a larger wavelength range is more desirable since it gives more discernable features. Stacking multiple sensors (102) to probe a wider range is possible but is more expensive and leads to more complicated system designs. Since the tuning capability of commercially available distributed feedback (DFB) lasers provides ~20 $cm^{-1}$ of spectral range, one may assess the effect of spectral range on the sensor's performance by calibrating to different multiples of 20 $cm^{-1}$ segments of range. The experiments summarized in Table 1, below, show that the minimal use of two lasers (100) staggered at [5400-5420] U [5900-5920] $cm^{-1}$ gives comparable results to the use of 30 sensors (102) to cover the whole range. The results are displayed as error percentages for estimated WC and GF when minimizing the objective function presented below in Equation 3, both with and without $L_s$, the error term related to synthetically generated data (defined below). Many of the results shown in the figures presented in this document are thus calibrated to this small range.

TABLE 1

| Experiment details | | | Baseline error (%) | | Baseline + $L_s$ error (%) | |
|---|---|---|---|---|---|---|
| Exp. # | Range [$cm^{-1}$] | # lasers | WC | GF | WC | GF |
| 1 | [5690-5710] | 1 | 28.95 | 4.98 | 32.13 | 2.89 |
| 2 | [5680-5720] | 2 | 23.38 | 1.77 | 24.1 | 0.71 |
| 3 | [5400-5420]U[5900-5920] | 2 | 3.14 | 0.8 | 1.26 | 1.21 |
| 4 | [5640-5760] | 6 | 13.4 | 1.34 | 15.55 | 1.06 |
| 5 | [5400-5420]U[5500-5520]U[5600-5620]U [5700-5720]U[5800-5820]U[5900-5920] | 6 | 2.4 | 1.24 | 1.9 | 0.84 |
| 6 | [5400-6000] | 30 | 2.18 | 1.62 | 1.19 | 0.54 |

Note that the wavelengths considered in Table 1 do not encompass all viable values. For example, water features also dominate around 7000 cm-1 and oil surrogate features are strong around 4600 cm-1 (not shown). Extending to non-infrared bandwidths may also be possible, although distributed feedback (DFB) lasers might not be applicable there. To summarize, the model is agnostic to wavelength and only requires discernable water/oil features; to the extent that technology allows for the detection of water/oil features, the methods described herein may be applied.

Figure 1C:
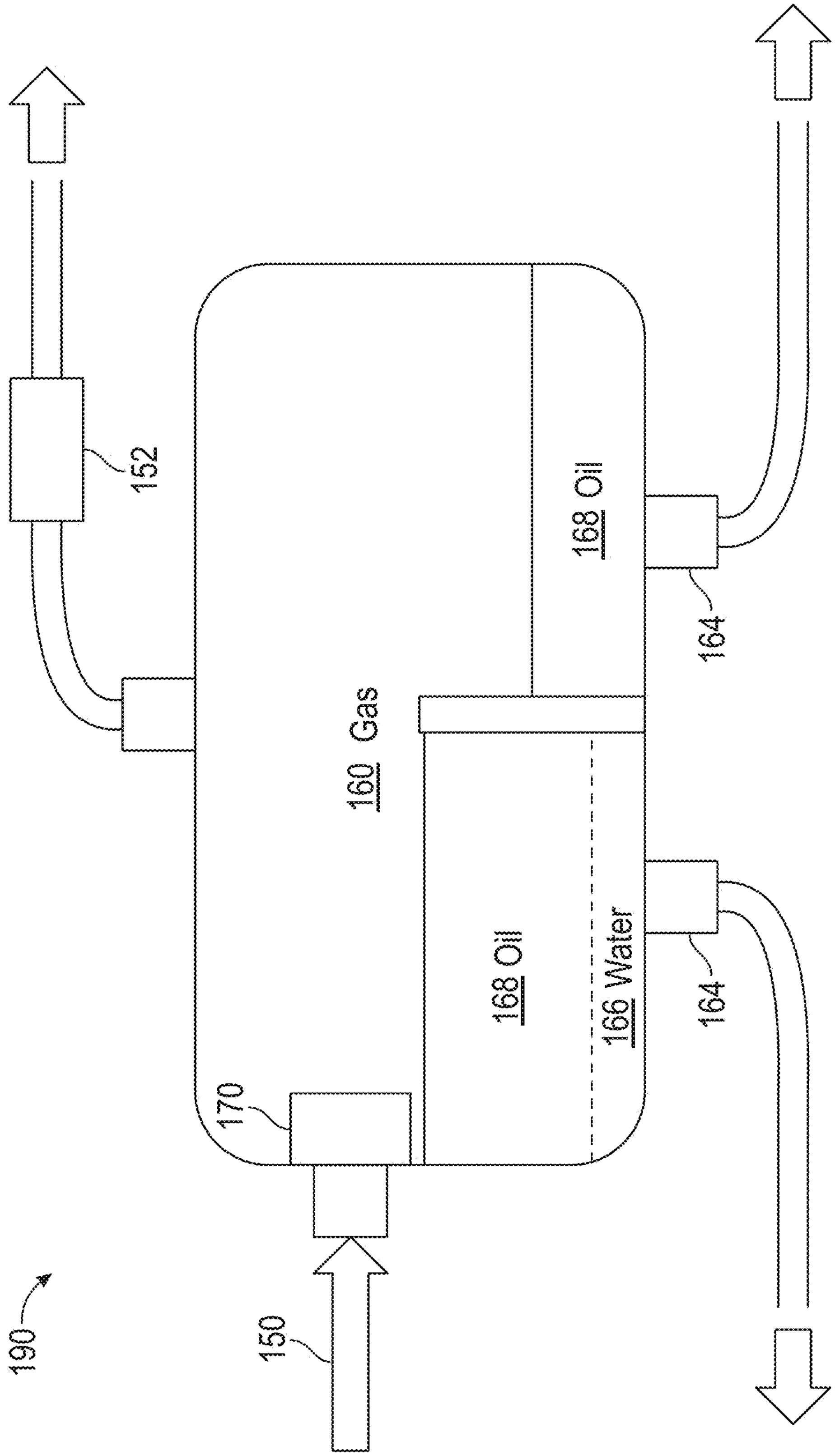
FIG. 1C shows a three-phase separator, in accordance with one or more embodiments.

FIG. 1C depicts an example of a gas-oil separator (190), in which a water-cut laser sensor (170) may be installed and used. The gas-oil separator (190) includes a vessel that separates fluids extracted from wells into gas and liquids. Separators may be two phase or three-phase. The former only separates gas from liquid while the latter further separates water from oil. FIG. 1C represents a three-phase separator.

A mix of gas and fluids coming from a well may enter the separator through an inlet (150). A mixed emulsion of vaporized liquids and gas (160) exits through the top of the vessel, where the vaporized liquids may be removed with a mist extractor (152). Turbulent flow allows gas bubbles to escape more quickly than laminar flow. Gravity acts as the main force separating the liquids into water (166) and oil (168). Lighter fluids, such as oil, float while the heavier fluids, such as water and brine, sink to the bottom. The different fluids then exit the vessel through exit valves (164) at the bottom. The amount of gas/liquid separation is a function of factors including the separator's operating pressure and temperature, the length of time of the fluids have remained mixed, and the type of flow of the fluid (turbulent versus laminar). A water-cut laser sensor (170) may be placed, for example, near the inlet (150) of the fluid mixture (104) into the gas-oil separator (190). From there, the pressure, temperature, and other variables may be adjusted based on the readings of the water-cut laser sensor (170) to allow for optimal separation.

Before presenting the proposed invention in further detail, the essential elements of a machine learning model are presented for context.

Figure 2:
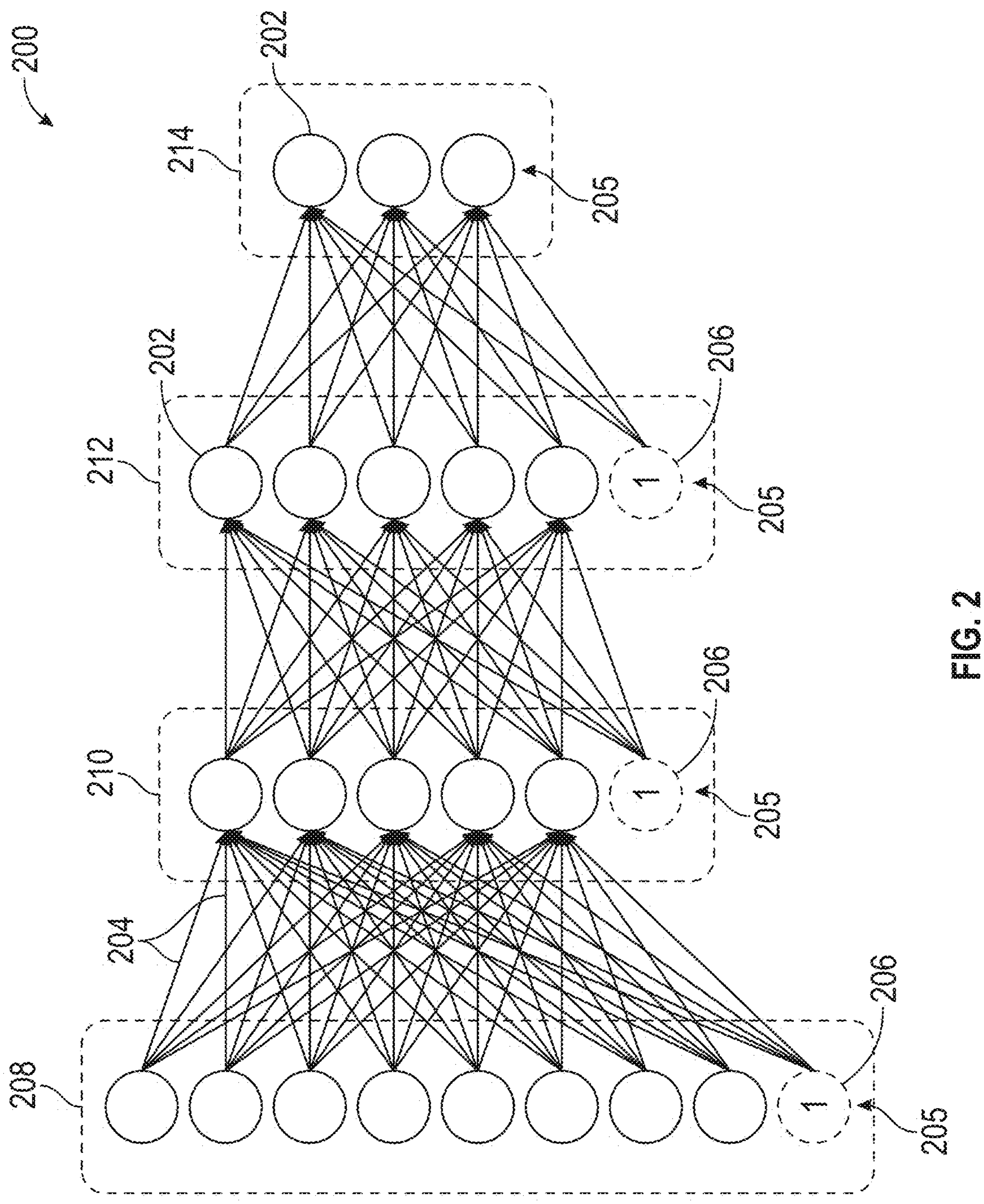
FIG. 2 shows a neural network, in accordance with one or more embodiments.

FIG. 2 shows a neural network, a common ML architecture for prediction/inference. At a high level, a neural network (200) may be graphically depicted as comprising nodes (202), shown here as circles, and edges (204), shown here as directed lines connecting the circles. The nodes (202) may be grouped to form layers, such as the four layers (208, 210, 212, 214) of nodes (202) shown in FIG. 2. The nodes (202) are grouped into columns for visualization of their organization. However, the grouping need not be as shown in FIG. 2. The edges (204) connect the nodes (202). Edges (204) may connect, or not connect, to any node(s) (202) regardless of which layer (205) the node(s) (202) is in. That is, the nodes (202) may be fully or sparsely connected. A neural network (200) will have at least two layers, with the first layer (208) considered as the "input layer" and the last layer (214) as the "output layer." Any intermediate layer, such as layers (210) and (212) is usually described as a "hidden layer." A neural network (200) may have zero or more hidden layers, e.g., hidden layers (210) and (212). However, a neural network (200) with at least one hidden layer (210, 212) may be described as a "deep" neural network forming the basis of a "deep learning model." In general, a neural network (200) may have more than one node (202) in the output layer (214). In this case the neural network (200) may be referred to as a "multi-target" or "multi-output" network.

Nodes (202) and edges (204) carry additional associations. Namely, every edge is associated with a numerical value. The numerical value of an edge, or even the edge (204) itself, is often referred to as a "weight" or a "parameter." While training a neural network (200), numerical values are assigned to each edge (204). Additionally, every node (202) is associated with a numerical variable and an activation function. Activation functions are not limited to any functional class, but traditionally follow the form:

$$A = f\left(\sum_{i\in(incoming)}[(\text{node value})_i(\text{edge value})_i]\right), \tag{2}$$

where i is an index that spans the set of "incoming" nodes (202) and edges (204) and $f$ is a user-defined function. Incoming nodes (202) are those that, when viewed as a graph (as in FIG. 2), have directed arrows that point to the node (202) where the numerical value is computed. Functional forms of $f$ may include the linear function $f(x)=x$, sigmoid function $$f(x) = \frac{1}{1+e^{-x}},$$

and rectified linear unit function $f(x)=\max(0,x)$, however, many additional functions are commonly employed in the art. Each node (202) in a neural network (200) may have a different associated activation function. Often, as a shorthand, activation functions are described by the function $f$ by which it is composed. That is, an activation function composed of a linear function $f$ may simply be referred to as a linear activation function without undue ambiguity.

When the neural network (200) receives an input, the input is propagated through the network according to the activation functions and incoming node (202) values and edge (204) values to compute a value for each node (202). That is, the numerical value for each node (202) may change for each received input. Occasionally, nodes (202) are assigned fixed numerical values, such as the value of 1, that are not affected by the input or altered according to edge (204) values and activation functions. Fixed nodes (202) are often referred to as "biases" or "bias nodes" (206), and are depicted in FIG. 2 with a dashed circle.

In some implementations, the neural network (200) may contain specialized layers (205), such as a normalization layer, or additional connection procedures, like concatenation. One skilled in the art will appreciate that these alterations do not exceed the scope of this disclosure.

As noted, the training procedure for the neural network (200) comprises assigning values to the edges (204). To begin training, the edges (204) are assigned initial values. These values may be assigned randomly, assigned according to a prescribed distribution, assigned manually, or by some other assignment mechanism. Once edge (204) values have been initialized, the neural network (200) may act as a function, such that it may receive inputs and produce an output. As such, at least one input is propagated through the neural network (200) to produce an output. Recall that a given data set will be composed of inputs and associated target(s), where the target(s) represent the "ground truth," or the otherwise desired output. The neural network (200) output is compared to the associated input data target(s). The comparison of the neural network (200) output to the target(s) is typically performed by a so-called "loss function"; although other names for this comparison function such as "error function" and "cost function" are commonly employed. Many types of loss functions are available, such as the mean-squared-error function. However, the general characteristic of a loss function is that it provides a numerical evaluation of the similarity between the neural network (200) output and the associated target(s). The loss function may also be constructed to impose additional constraints on the values assumed by the edges (204), for example, by adding a penalty term, which may be physics-based, or a regularization term. Generally, the goal of a training procedure is to alter the edge (204) values to promote similarity between the neural network (200) output and associated target(s) over the data set. Thus, the loss function is used to guide changes made to the edge (204) values, typically through a process called "backpropagation."

The loss function will usually not be reduced to zero during training. And, once trained, it is not necessary or required that the neural network (200) exactly reproduce the output elements in the training data set when operating upon the corresponding input elements. Indeed, a neural network (200) that exactly reproduces the output for its corresponding input may be perceived to be "fitting the noise." In other words, it is often the case that there is noise in the training data, and a neural network (200) that is able to reproduce every detail in the output is reproducing noise rather than true signal. The price to pay for using such a "perfect" neural network (200) is that it will be limited to fitting only the training data and not able to generalize to produce a realistic output for a new and different input that has never been seen by it before.

The proposed machine learning model in this disclosure may consist of an autoencoder system that minimizes the difference between input measured mixture absorbance spectra and their reconstruction. An autoencoder is composed of an encoder and decoder. The encoder typically reduces the dimension of the input to the autoencoder down to a few parameters. Conversely, the decoder expands the reduced number of parameters to reproduce the input. The reduced set of parameters produced by the encoder may have physical or explanatory meaning, as they do in this application. A measure of quality of the autoencoder may be its ability to reproduce the input after passing through both the encoder and the decoder.

In some embodiments, the encoder and the decoder may be the inverse of each other. However, in other embodiments, such as the example embodiment described in detail below, they may be very different functions. The purpose of the encoder in this disclosure is to map a measured spectrum from one fluid mixture (104) to its estimated water-cut (denoted, $\overline{WC}$) and path-length (denoted, $\overline{PL}$) fraction values.

Figure 3:
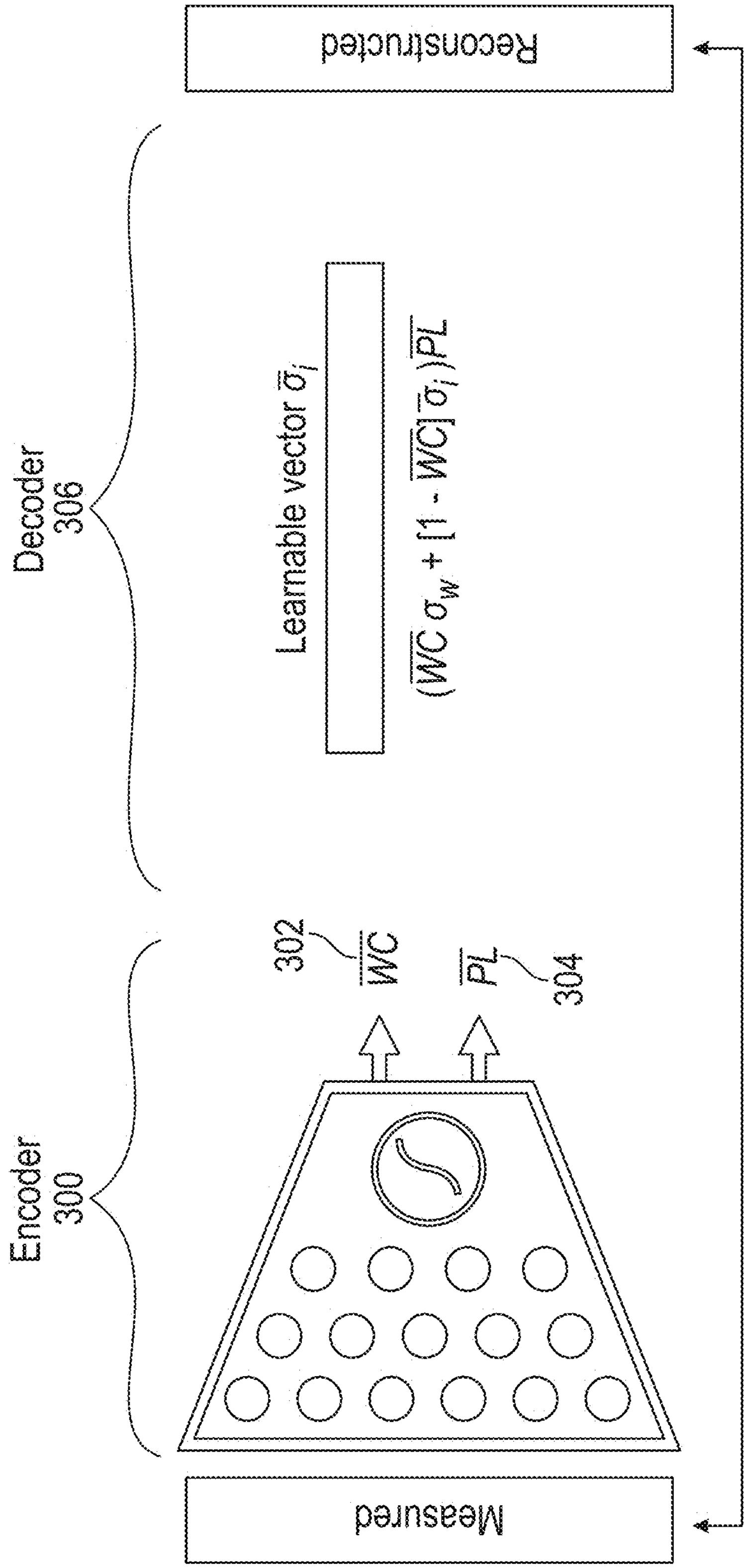
FIG. 3 shows an autoencoder with an encoder and a decoder, in accordance with one or more embodiments.

FIG. 3 shows an embodiment of the structure of the proposed autoencoder. The encoder (300) is similar to the network of FIG. 2. In some embodiments, encoder (300) may utilize a neural network (200) with fully connected layers, rectified linear unit (ReLU) activation functions, and a sigmoid function at the last layer to restrict the output range to be between 0 and 1 (as required for the $\overline{WC}$ (302) and $\overline{PL}$ (304) parameters).

Conventionally, pairs of mixture spectra and their labels (i.e., the known corresponding water-cut and path-length fraction values) are used to train a network in a supervised setting. This, however, requires manual calibration, since samples need to be tested to produce training examples. However, the novel invention disclosed herein avoids manual calibration of labelled mixture spectra. The encoder (300) is calibrated based on the signal produced by the decoder (306). The decoder's objective is to reconstruct the input mixture spectra based on the Beer-Lambert law which may be written as follows:

$$\overline{A}_{rec} = \left[\overline{WC}\cdot\sigma_w + \left(1-\overline{WC}\right)\cdot\sigma_l\right]\cdot\overline{PL}, \qquad \text{Eq. (1)}$$

where $\overline{WC}$ (302) and $\overline{PL}$ (304) are the estimated water-cut and path-length fraction values from the encoder (300), $\sigma_w$ is the known absorption cross-section of (fresh) water, and $\overline{A}_{rec}$ is the resulting absorbance spectrum. The learned interference absorption cross-section will be denoted as $\overline{\sigma}_i$ in this document.

It should be understood that $\sigma_w$ and $\overline{\sigma}_l$, are functions of the wavenumber, ν (i.e., the independent variable of the absorbance spectrum). Thus, the observed absorbance spectrum may be a linear combination of two spectra, one due to the water in the mixture of fluids, the other due to the oil. The water-cut determines the proportion of each spectrum in the measured combination and is an output of the encoder (300). Gas fraction also has a spectrum, but gases are weak absorbers compared to liquids. So, while the gas will indeed have some contribution to absorbance, its magnitude will be very small. It is assumed that this small amount is negligible and will not interfere with measurement.

It is the case that a more complex, nonlinear relationship may be defined between path length, water-cut and the measured spectrum using a general quadratic blending equation:

$$\overline{A_{rec}} = \left(\left(1-\overline{f_l}\right)\sigma_w + \overline{f_l}\overline{\sigma_l}\right)\overline{PL}$$

where $\overline{f}_l = \overline{a}[1-\overline{WC}]^2 + \overline{b}[1-\overline{WC}]$ and $\overline{a}+\overline{b}-1$. However, for the embodiments contained within this document, only a linear relationship is used.

In this document, a bar over a given variable denotes that it is the estimated counterpart from a theoretical model. For example, WC would be the observed water-cut in the real world, while $\overline{WC}$ is its estimated value given by the model.

The Beer-Lambert Law, shown in Equation 1, is obtained by taking a logarithmic measure of the amount of light absorbed (as a function of wavelength) and, for Equation 1, is obtained as follows: $A_{meas}(\nu) = -\ln(I_t/I_0) - (WC\cdot\sigma_w(\nu) + [1-WC]\cdot\sigma_i(\nu))(L[1-GF])$, where $I_t$ and $I_0$ are the transmitted and incident light intensities respectively, and ν is the wavelength. L is the total length and is a known constant for a given experimental setup. The gas fraction is a function of the path length $$\left(GF = \frac{L = PL}{L}\right).$$

Since L is known, knowing one of either GF or PL implies knowing the other. In this way, both water-cut and gas fraction values are estimated through a calibrated autoencoder.

It is known by people of ordinary skill in the art that brine and solids may cause a baseline shift in a peak of the absorbance spectrum. However, the model presented in this document allows for robust estimation against these effects. If, for example, the salinity of water does not change significantly with time, then the model will estimate $\sigma_i - \sigma_{oil}\sigma_{salt}$. In other words, the model is capable of calibrating to fresh water vs. a mixture of other things (which may include oil, salt, silt, etc.), given that the concentration of these interfering components doesn't drastically change in a short timeframe. Alternatively, one may solve for $\bar{\sigma}_w$ in a similar way to the model for solving for $\bar{\sigma}_i$.

The independent variable of an absorbance spectrum in Equation 1 is the wavelength, ν, of the laser light used to analyze it. (See FIG. 1B.) Its dependent variable is the actual absorbance value. The unknown in the equation is $\bar{\sigma}_I$, the absorption cross-section of the interference, which is set in the decoder (306) as a learnable vector. Thus, the decoder (306) follows a physical relationship when converting $\overline{WC}$ (302), $\overline{PL}$ (304), and $\bar{\sigma}_I$ into absorbance mixture spectra, whereas the encoder (300) may be implemented as a general-purpose neural network (200). In this way, the autoencoder system tries to fit data to the Beer-Lambert law through the decoder (306). In doing so, the decoder (306) calibrates the encoder (300) to accurately determine the water-cut and path-length fraction value depending solely on mixture data from the field.

WC and PL are not independent variables. The two are simply related by $$WC = \frac{l_w}{PL},$$

where PL=$l_w$+$l_o$. In other words, WC is nothing but the ratio of the length at which water is absorbed to the total length of water and oil. If that ratio is one (i.e., the path length is only traveled in water), then the WC is at 100%. If the path length is zero (i.e., the flow is purely gaseous) then the WC is undefined (this is due to the definition, $$\left. WC = \frac{l_w}{l_w + l_o} \right).$$

To solve for absolute percentage of any phase in the flow, one may divide the length at which the phase is absorbing by the total length. To obtain the percentage of oil one may subtract WC from 100. The length at which gas is absorbing is $l_g$=L−PL. Finally, the length at which oil is absorbing $l_o$=L−$l_w$−$l_g$. To get any absolute percentage, one must divide by the total length L (i.e., Water %=Lw/L; Oil %=$l_o$/L; Gas %=$l_g$/L=GF). Note that WC and PL are determined from the model, and L is a known parameter.

More specifically, GF=(L−PL)/L, where L is known. Therefore, knowing one of PL or GF, the other variable may be solved for. However, WC=$l_w$/PL, where $l_w$ is not known. Thus $l_w$ needs to be determined. In summary, two quantities must be determined, either WC and PL, or $l_w$ and $l_g$. Other quantities may be derived from whichever pair is determined.

To reduce the dependence on real data, the synthetic data used to train the autoencoder may be generated based on the known and reconstructed absorption spectra ($\sigma_w$ and $\bar{\sigma}_I$). Synthetic spectra data produced by random labels ($\overline{WC}$ (302) and $\overline{PL}$ (304)) can thus be used for a supervised loss on the encoder (300), where the mean squared error between estimated and randomly assigned water-cut and path-length fraction values is minimized. When using the synthetic loss ($L_s$), a batch of synthetic data may be generated for each batch of real data the model uses for training. The total loss can thus be written as the sum of the main and synthetic loss:

$$\mathcal{L} = L_m + \lambda L_s, \quad \text{Eq. (2)}$$

$$\mathcal{L} = \mathbb{E}_{x \sim p_{meas}}\left[\|x - d_\phi(e_\theta(x))\|_2^2\right] + \lambda \mathbb{E}_{\hat{x},\hat{z} \sim p_{synth}}\left[\|\hat{z} - e_\theta(\hat{x})\|_2^2\right], \quad \text{Eq. (3)}$$

where $e_\theta$ is the encoder (300) parameterized by θ, and $d_\phi$ is the decoder (306) parameterized by ϕ, with data (i.e., measured spectra x and synthetic spectra/target pairs [$\hat{x}$, $\hat{z}$]) drawn from the measured and synthetic distributions ($p_{meas}$ and $p_{synth}$, respectively). Note that in some embodiments, $p_{synth}$ may be chosen to be a uniform distribution on the full dynamic range (0-100% for both water-cut and path-length fraction value). In other embodiments, $p_{synth}$ may be chosen from another probability distribution, or by another method that does not have a well-defined probability distribution. λ is a tradeoff parameter that adjusts the emphasis on each of the objective functions.

To summarize: training the autoencoder requires minimizing $\mathcal{L}$ using a set of real data and a set of synthetic data. The synthetic data may include randomly generated labels, $\hat{z}$ (which are $\overline{WC}$ (302) and $\overline{PL}$ (304)), and associated synthetic spectra, $\hat{x}$, produced by the Beer-Lambert Law. The real data include training mixture spectra, x, observed from real fluid samples. During training, θ and ϕ (the node weights in the neural network (200) and $\bar{\sigma}_I$, the absorption cross-section (spectrum) of the interference) are modified to minimize $\mathcal{L}$. Since a common set of parameters is being optimized in both parts of Eq. 3, the minimization using the measured and synthetic data must be done at the same time. Once minimized, the optimal weights may be used to convert newly obtained observed measured spectra into an estimate of $\overline{WC}$ (302) and $\overline{PL}$ (304).

One may think of the two losses in Eq. 3 as being complementary. As the main loss, $L_m$, calibrates to the real world, the secondary synthetic loss, $L_s$, generalizes the results to the full dynamic range.

The results currently discussed in this document focus on silicone oil as the interferent, so only mixtures of water and oil may be discussed to avoid confusion. $\bar{\sigma}_i$ can be generalized to a matrix corresponding to a list of unknown interferents. Optimization becomes more challenging as the number of interferents increases. That said, if the concentrations of these species are not changing drastically in a given time window, the model can continuously calibrate, adjusting to the changing $\sigma_i$.

Silicone oil is used as the main interferent in this example, while variations in oil composition are modeled by adding contributions from octane, methanol, isopropanol, and ethanol. Synthetic mixtures are randomly generated according to:

$$A_{meas} = (WC \cdot \sigma_w + [1 - WC] \cdot \sigma_o)(L[1 - GF]) \quad \text{Eq. (4)}$$

where L is the total length and GF is the gas fraction. Equation 4 is very similar to Equation 1. The main difference is that Equation 4 is measured, while Equation 1 is reconstructed. In addition, Equation 4 provides a method to simulate data. Calibration data recently observed in the field may be split into training and validation data sets; newly obtained data points are test data. Training and validation data (which can be lumped together as calibration data) are created from the same distribution, while the test data is simulated from a separate distribution that may be different.

The validation data set is used to avoid over-fitting, while the test set is used to evaluate the performance of the model. In both cases, additional synthetic data may be created for use with the synthetic loss function, based on the approximate $\overline{\sigma}$ in the decoder (306).

The autoencoder for this example is trained on a calibration set of 1200 randomly generated samples (from a uniform distribution) where 80% was used for training and 20% for validation. A separate set of 1000 uniformly random observations were used for testing. The full dynamic range considered in the experiments is 1-100% for both water-cut and path-length fraction value.

Figure 4A:
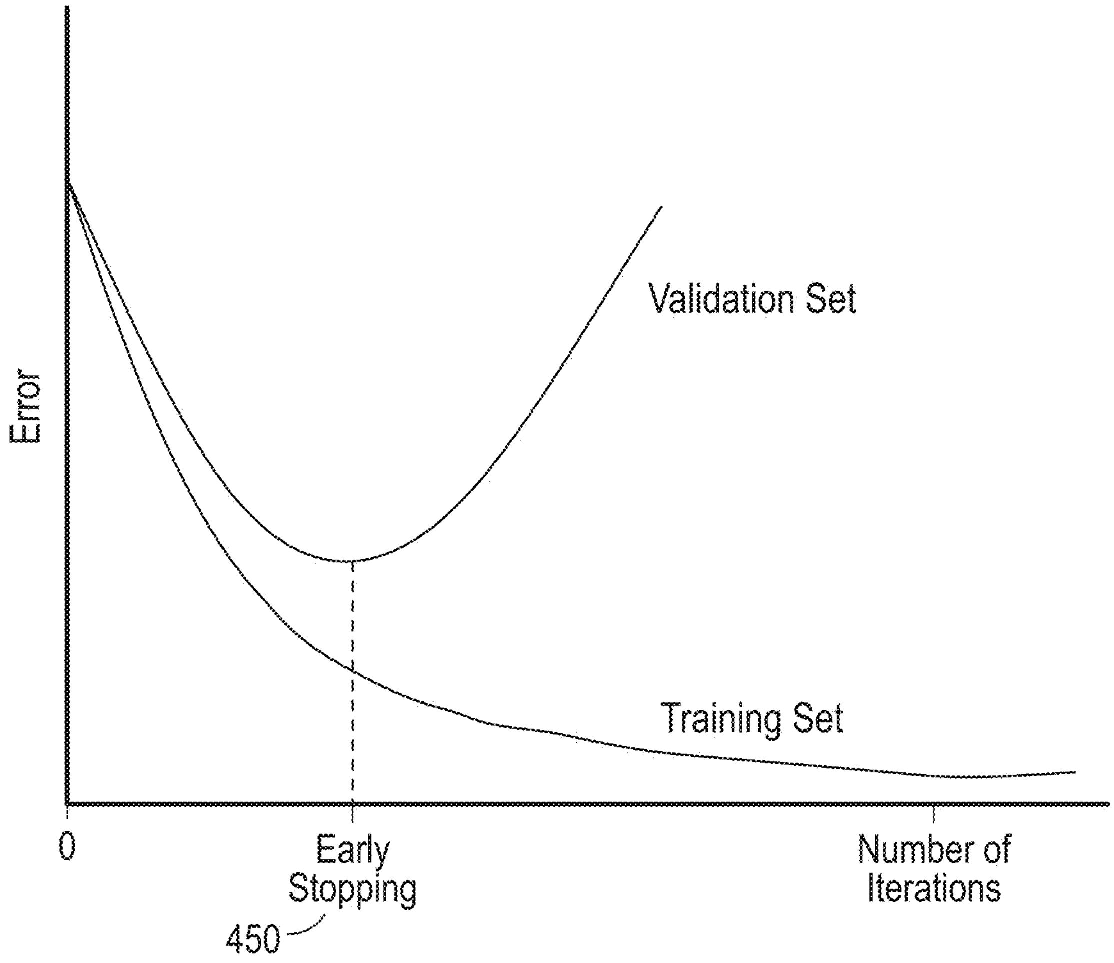
FIG. 4A shows the error resulting from applying a trained autoencoder to estimate water-cut and path-length fraction values, in accordance with one or more embodiments.

In this example, both the encoder (300) and decoder (306) use an Adam optimizer where the learning rate of the encoder (300) is set to 0.01 and the decoder's learning rate is set to 0.001 (to force fast reactivity from the encoder (300)). The learning rate controls how fast the weights of the model are changed. If it is set to a low value, the weights of the model will not drastically change and stay relatively close to where they start. If it is set to a high value, the weights will quickly react to changing inputs—this is desirable in the encoder since it is waiting for the signal from the decoder. A batch size of 128 is used as a step scheduler that decays the learning rate by a factor of 0.1 every 100 epochs. An epoch is one complete pass through the entire training dataset. The batch size is the number of samples used in one forward and backward pass through the autoencoder network. The "backward pass" in this case refers to the process of using backpropagation to estimate gradients and change the weights of the neural network. This process is repeated over several epochs until the model weights converge. Hyperparameters used in this process are the learning rates, architecture of the encoder (300), batch size, scheduler rate, and number of epochs. The same hyperparameters are used for all tests to guarantee a fair comparison between different cases, and to mimic operating conditions where tuning is not afforded. Early stopping (450) rules are used for all models to prevent over-fitting. Over-fitting may be noticed if a reduction of training loss does not correspond to a reduction of validation loss as shown in FIG. 4A. Early stopping is used whenever the model that minimized the error on the validation set is chosen to calibrate the water-cut laser sensor (170).

Figure 4B:
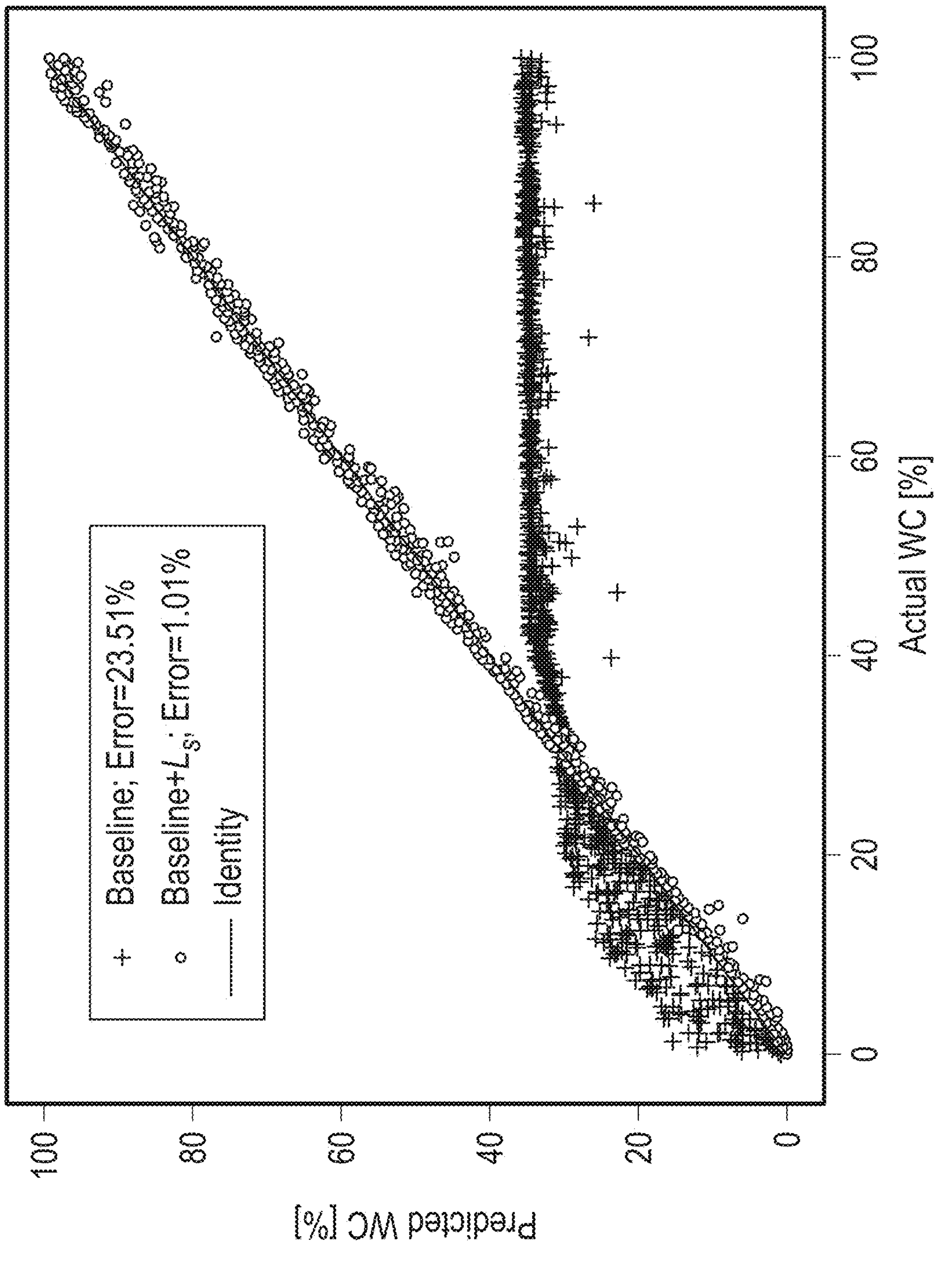
FIG. 4B shows convergence of a method, in accordance with one or more embodiments.
Figure 4C:
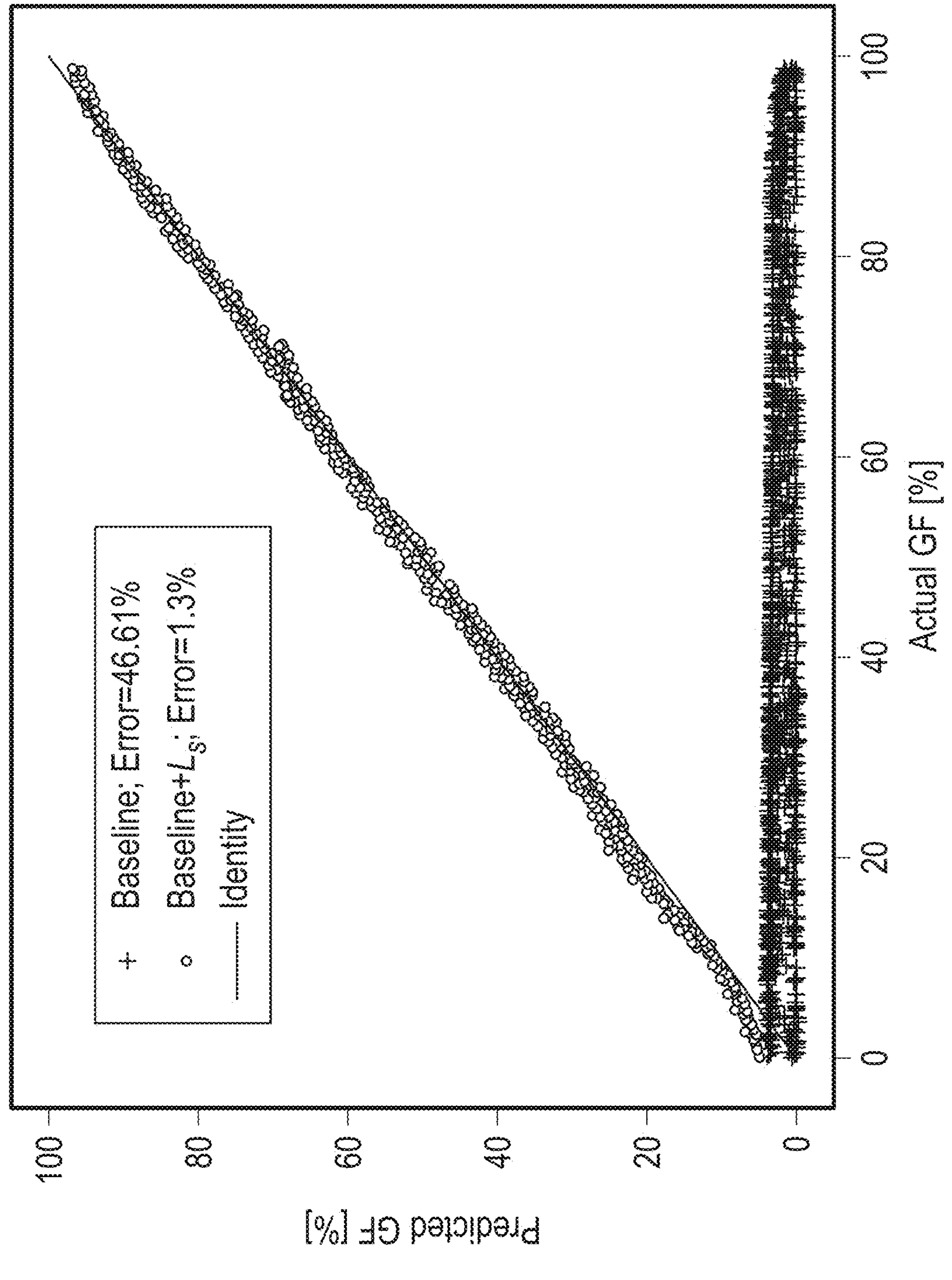
FIG. 4C shows convergence of a method, in accordance with one or more embodiments.

FIGS. 4B and 4C show examples of the results of applying the trained autoencoder on mixture spectra from a number of observations. Each dot and cross is a test case where the calibrated (i.e., trained) autoencoder predicts either a water-cut (FIG. 4B) or a gas fraction (FIG. 4C). Crosses in either figure correspond to not using the synthetic loss ($L_s$), while dots correspond to including it. A perfect fit corresponds to the diagonal lines in FIGS. 4B and 4C. In particular, these figures show the importance of using a synthetic loss ($L_s$) to overcome dynamic range biases. Dynamic range biases refer to the situation where the calibration data (used for training/validation) comes from a distribution that does not match that of the test data. In the specific examples shown in FIGS. 4B and 4C, a range of 0-10% is used for the water-cut, and 0% for the gas fraction for the calibration data, while the full dynamic range (i.e., 0-100% water-cut and 0-100% gas fraction) is used for the test data.

To reiterate, in FIG. 4B, the estimated $\overline{\text{WC}}$ (vertical axis) is compared with the actual WC (horizontal axis). The diagonal line represents a perfectly accurate estimation of $\overline{\text{WC}}$ (302) from the data. When the method is applied to the synthetic observations and the synthetic loss function, $L_s$, is used, the estimation values are close to the diagonal line. However, when only $L_m$ is used, the estimation results are far from the diagonal line. Similarly, for FIG. 4C, the estimated gas fraction (or, equivalently, $\overline{\text{PL}}$ (304)) is on the vertical axis and the actual gas fraction (or PL (304)) is on the horizontal axis. The diagonal line again represents a perfectly accurate estimation of gas fraction (or $\overline{\text{PL}}$ (304)). As for $\overline{\text{WC}}$ (302), when $L_s$ is used, the estimation results are highly accurate. Conversely, when not used, the results are far from ideal, as shown by the cluster of points near the x-axis. The example shown in FIGS. 4B and 4C uses 1200 samples of 0-10% WC and 0% GF for calibration, and 1000 samples of 0-100% WC and 0-100% GF for testing—i.e., uniformly random observations.

Figure 5:
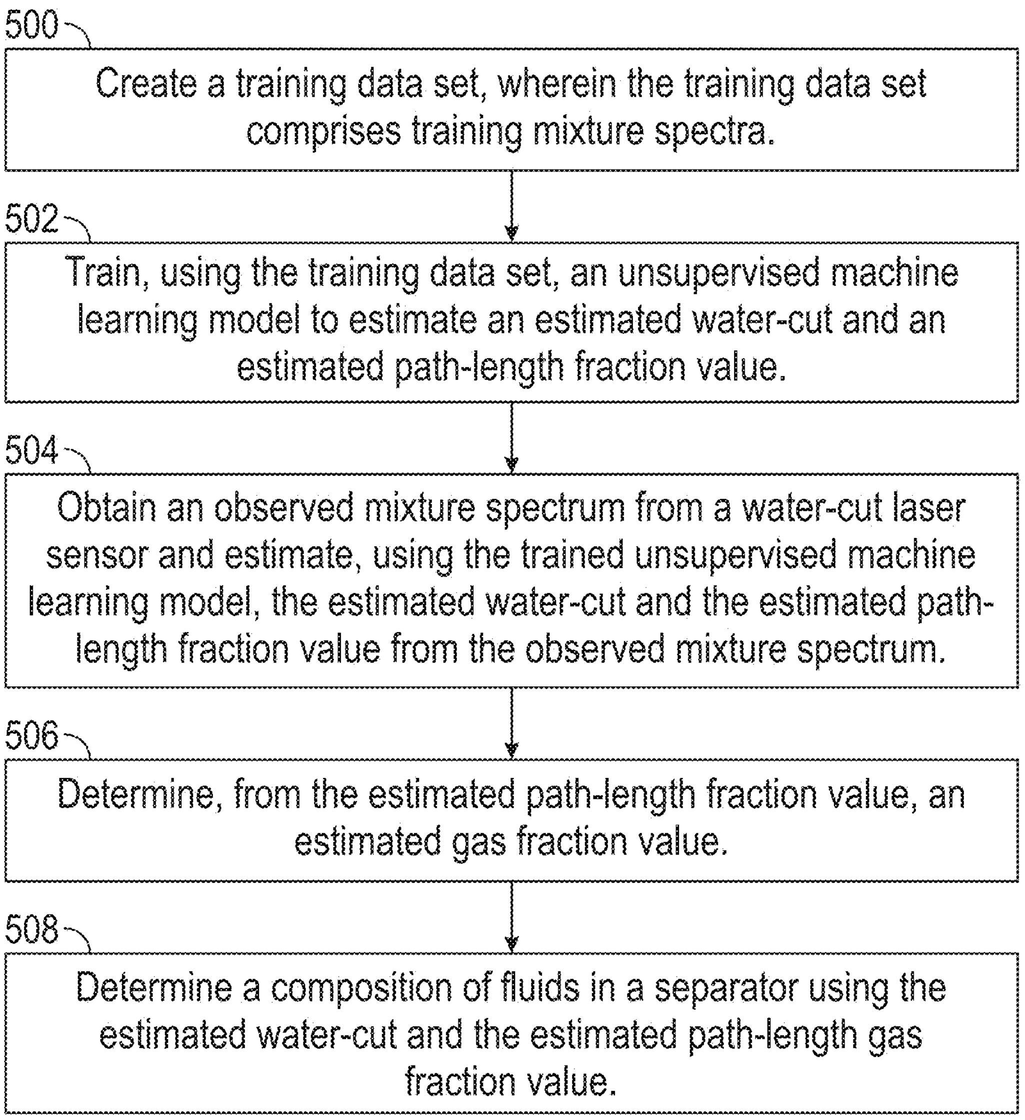
FIG. 5 shows a workflow, in accordance with one or more embodiments.

FIG. 5 presents the steps of the methodology presented above. In Step (500), a training data set is created. The training data set may include both real and synthetic data. The real data comes in the form of spectra obtained by a water-cut laser sensor (170) applied to a mixture of fluids. The fluids may include gas, water, and oil. The synthetic data include synthetic values of water-cuts and synthetic path-length fraction values randomly drawn from a uniform distribution between zero and one (the labels), and synthetic absorbance spectra generated from these labels using the Beer-Lambert law.

In Step (502), an unsupervised machine learning model is trained to predict an estimated water-cut and an estimated path-length fraction value. Through the training process, the edge weights of a neural network (200) are modified, as well as an absorption cross-section. Through the process of training, the unsupervised machine learning model may be understood to be self-calibrating.

The self-calibrating unsupervised machine learning model used for the prediction may be an autoencoder. The autoencoder, in turn, may include an encoder (300) and a decoder (306) as separate components. The encoder (300) may utilize fully connected rectified linear activation functions at each node of its network and a sigmoid function at its last layer to ensure that its output remains between 0 and 1. The encoder (300) produces values for water-cut and path-length fraction values from an input absorbance spectrum. The decoder (306) may utilize the water-cut and path-length fraction value to reproduce an absorption spectrum using the Beer-Lambert law.

The unsupervised machine learning model may be applied to three-phase flows and may be continuously adapted to prevent senor drift. In this way, the water-cut laser sensor (170) may retain its ability to accurately predict water-cuts and path-length fraction values from spectra. The continuous adaptation proceeds by retraining the autoencoder according to the procedure above as more measurements arrive. In other words, the continuous adaptation is achieved by retraining the unsupervised machine learning model at user-specified intervals; each retraining corrects for sensor drift and allows for more accurate estimation of parameters being optimized. The number of measurements to use for retraining, the number of synthetic labels to create and model with the Beer-Lambert Law, and the frequency of retraining may be application dependent.

The unsupervised machine learning model may be trained by simultaneously minimizing two objective functions. The first objective function pertains to observed training measured spectra, while the second objective function pertains to synthetic water-cut, synthetic path-length fraction values, and (from them) synthetic spectra. An Adam optimizer may be used to accelerate convergence rate of the minimization of the combined objective function for training of the unsupervised machine learning model.

The synthetic water-cuts and synthetic path-length fraction values may be drawn from a uniform distribution. The synthetic measured spectra are generated from the synthetic water-cuts and synthetic path-length fraction values through the Beer-Lambert law.

In Step (504), an absorption spectrum of a fluid mixture (104) may be observed by a water-cut laser sensor (170). The unsupervised machine learning model may then take the spectrum and estimate an estimated water-cut and an estimated path-length fraction value. Furthermore, a composition of the fluids may be determined from the estimated water-cut and estimated path-length fraction value.

When the composition of fluids is referred to, it's the simple case of water and interferent. The equations above, as currently written, do not separate between multiple interferents. For example, the autoencoder cannot tell one what the composition of oil is (could be made up of hundreds of species). The model will, however, give an estimated infrared spectrum of the mixture of interferents which may give physical insight on what's in the oil. However, the equations may be expanded to N number of interfering species.

In Step (506), the estimated path-length value may be converted to a gas fraction value using the methods described above. And, in Step (508), the methodology may be applied to fluids obtained in a separator, thereby predicting the mixture of fluids.

Figure 6:
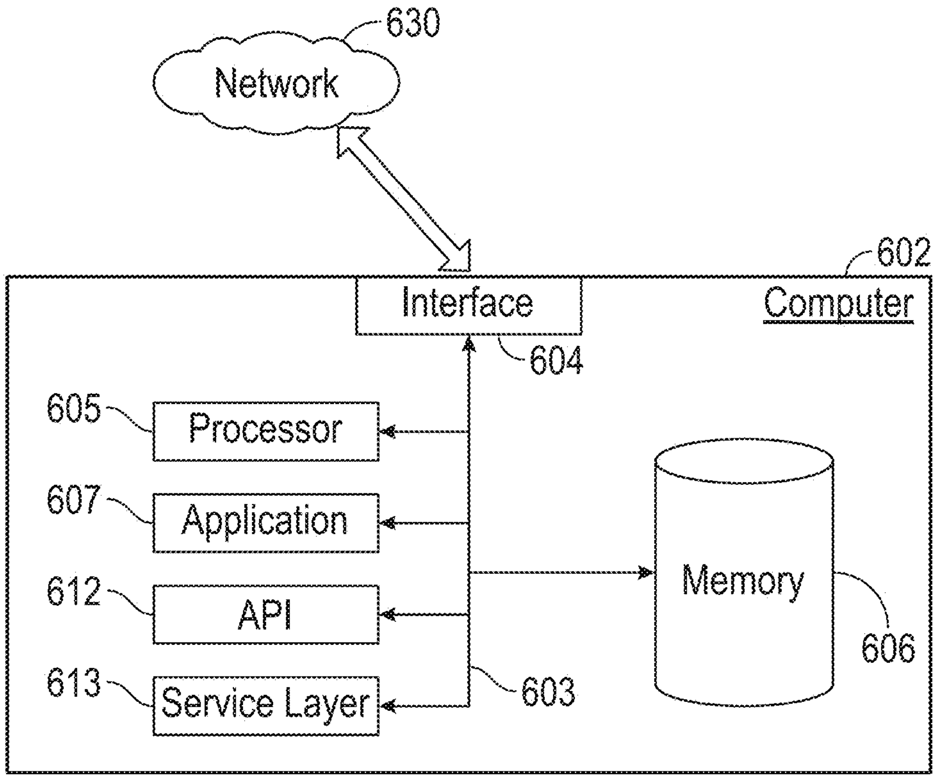
FIG. 6 shows a computer system, in accordance with one or more embodiments.

The unsupervised machine learning model may be implemented on a general-purpose computing system. FIG. 6 depicts a block diagram of a such a computer system used to provide computational functionalities associated with described algorithms, methods, functions, processes, flows, and procedures as described in this disclosure, according to one or more embodiments. The illustrated computer (602) is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. The illustrated computer (602) may also encompass custom-designed neural networks (200), as well as graphics processing units (GPUs). Additionally, the computer (602) may include an input device, such as a keypad, keyboard, touch screen, or other device that can accept user information, and an output device that conveys information associated with the operation of the computer (602), including digital data, visual, or audio information (or a combination of information), or a GUI.

The computer (602) can serve in a role as a client, network component, a server, a database or other persistency, or any other component (or a combination of roles) of a computer system for performing the subject matter described in the instant disclosure. The illustrated computer (602) is communicably coupled with a network (630). In some implementations, one or more components of the computer (602) may be configured to operate within environments, including cloud-computing-based, local, global, or other environment (or a combination of environments).

At a high level, the computer (602) is an electronic computing device operable to receive, transmit, process, store, or manage data and information associated with the described subject matter. According to some implementations, the computer (602) may also include or be communicably coupled with an application server, e-mail server, web server, caching server, streaming data server, business intelligence (BI) server, or other server (or a combination of servers).

The computer (602) can receive requests over network (630) from a client application (for example, executing on another computer (602)) and responding to the received requests by processing the said requests in an appropriate software application. In addition, requests may also be sent to the computer (602) from internal users (for example, from a command console or by other appropriate access method), external or third-parties, other automated applications, as well as any other appropriate entities, individuals, systems, or computers.

Each of the components of the computer (602) can communicate using a system bus (603). In some implementations, any or all of the components of the computer (602), both hardware or software (or a combination of hardware and software), may interface with each other or the interface (604) (or a combination of both) over the system bus (603) using an application programming interface (API) (612) or a service layer (613) (or a combination of the API (612) and service layer (613)). The API (612) may include specifications for routines, data structures, and object classes. The API (612) may be either computer-language independent or dependent and refer to a complete interface, a single function, or even a set of APIs. The service layer (613) provides software services to the computer (602) or other components (whether or not illustrated) that are communicably coupled to the computer (602). The functionality of the computer (602) may be accessible for all service consumers using this service layer. Software services, such as those provided by the service layer (613), provide reusable, defined business functionalities through a defined interface. For example, the interface may be software written in JAVA, C++, or other suitable language providing data in extensible markup language (XML) format or another suitable format. While illustrated as an integrated component of the computer (602), alternative implementations may illustrate the API (612) or the service layer (613) as stand-alone components in relation to other components of the computer (602) or other components (whether or not illustrated) that are communicably coupled to the computer (602). Moreover, any or all parts of the API (612) or the service layer (613) may be implemented as child or sub-modules of another software module, enterprise application, or hardware module without departing from the scope of this disclosure.

The computer (602) includes an interface (604). Although illustrated as a single interface (604) in FIG. 6, two or more interfaces (604) may be used according to particular needs, desires, or particular implementations of the computer (602). The interface (604) is used by the computer (602) for communicating with other systems in a distributed environment that are connected to the network (630). Generally, the interface (604) includes logic encoded in software or hardware (or a combination of software and hardware) and operable to communicate with the network (630). More specifically, the interface (604) may include software supporting one or more communication protocols associated with communications such that the network (630) or interface's hardware is operable to communicate physical signals within and outside of the illustrated computer (602).

The computer (602) includes at least one computer processor (605). Although illustrated as a single computer processor (605) in FIG. 6, two or more processors may be used according to particular needs, desires, or particular implementations of the computer (602). Generally, the computer processor (605) executes instructions and manipulates data to perform the operations of the computer (602) and any algorithms, methods, functions, processes, flows, and procedures as described in the instant disclosure.

The computer (602) also includes a memory (606) that holds data for the computer (602) or other components (or a combination of both) that can be connected to the network (630). For example, memory (606) can be a database storing data consistent with this disclosure. Although illustrated as a single memory (606) in FIG. 6, two or more memories may be used according to particular needs, desires, or particular implementations of the computer (602) and the described functionality. While memory (606) is illustrated as an integral component of the computer (602), in alternative implementations, memory (606) can be external to the computer (602).

The application (607) is an algorithmic software engine providing functionality according to particular needs, desires, or particular implementations of the computer (602), particularly with respect to functionality described in this disclosure. For example, application (607) can serve as one or more components, modules, applications, etc. Further, although illustrated as a single application (607), the application (607) may be implemented as multiple applications (607) on the computer (602). In addition, although illustrated as integral to the computer (602), in alternative implementations, the application (607) can be external to the computer (602).

There may be any number of computers (602) associated with, or external to, a computer system containing computers (602), wherein each computer (602) communicates over network (630). Further, the term "client," "user," and other appropriate terminology may be used interchangeably as appropriate without departing from the scope of this disclosure. Moreover, this disclosure contemplates that many users may use one computer (602), or that one user may use multiple computers (602).

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed is:

1. A method comprising:

creating a training data set, wherein the training data set comprises training mixture spectra;

training, using the training data set, an unsupervised machine learning model to estimate an estimated water-cut and an estimated path-length fraction value, wherein, via the training, the unsupervised machine learning model calibrates itself to determine the estimated water-cut and the estimated path-length fraction value;

obtaining an observed mixture spectrum from a water-cut laser sensor;

estimating, using the trained unsupervised machine learning model, the estimated water-cut and the estimated path-length fraction value from the observed mixture spectrum;

determining, from the estimated path-length fraction value, an estimated gas fraction value; and determining a composition of fluids in a separator using the estimated water-cut and the estimated gas fraction value.

2. The method of claim 1, wherein the training data set further comprises synthetic water-cuts, synthetic path-length fraction values, and synthetic measured spectra.

3. The method of claim 1, wherein the trained unsupervised machine learning model is an autoencoder.

4. The method of claim 3, wherein the autoencoder comprises an encoder and a decoder.

5. The method of claim 4, wherein the encoder utilizes a neural network with fully connected rectified linear activation functions and a sigmoid function at a last layer, and the decoder utilizes a Beer-Lambert Law.

6. The method of claim 4, wherein training the autoencoder comprises determining neural network node weights and an absorption cross-section.

7. The method of claim 1, wherein the trained unsupervised machine learning model applies to three-phase flows and may be continuously adapted to prevent sensor drift.

8. The method of claim 1, wherein an Adam optimizer is used to accelerate a convergence rate of the trained unsupervised machine learning model.

9. The method of claim 2, wherein the trained unsupervised machine learning model is trained by simultaneously minimizing a first objective function using the training mixture spectra, and a second objective function using the synthetic water-cuts, the synthetic path-length fraction values, and the synthetic measured spectra.

10. The method of claim 2, wherein the synthetic water-cuts and the synthetic path-length fraction values are drawn from a uniform distribution, and the synthetic measured spectra are generated from the synthetic water-cuts and the synthetic path-length fraction values using a Beer-Lambert Law.

11. A system, comprising:

a computer processor configured to:

create a training data set, wherein the training data set comprises training mixture spectra, train, using the training data set, an unsupervised machine learning model to estimate an estimated water-cut and an estimated path-length fraction value, wherein, via the training, the unsupervised machine learning model calibrates itself to determine the estimated water-cut and the estimated path-length fraction value, obtain an observed mixture spectrum from a water-cut laser sensor, estimate, using the trained unsupervised machine learning model, the estimated water-cut and the estimated path-length fraction value from the observed mixture spectrum, and determine a composition of fluids in a separator using the estimated water-cut and the estimated path-length fraction value, and determine, using the estimated path-length fraction value, an estimated gas fraction value.

12. The system of claim 11, wherein the training data set further comprises synthetic water-cuts, synthetic path-length fraction values, and synthetic measured spectra.

13. The system of claim 11, wherein the trained unsupervised machine learning model is an autoencoder.

14. The system of claim 13, wherein the autoencoder comprises an encoder and a decoder.

15. The system of claim 14, wherein the encoder utilizes fully connected rectified linear activation functions and a sigmoid function at a last layer, and the decoder utilizes a Beer-Lambert Law.

16. The system of claim 14, wherein training the autoencoder comprises determining neural network node weights and an absorption cross-section.

17. The system of claim 11, wherein the trained unsupervised machine learning model applies to three-phase flows and may be continuously adapted to prevent sensor drift.

18. The system of claim 11, wherein an Adam optimizer is used to accelerate a convergence rate of the trained unsupervised machine learning model.

19. The system of claim 12, wherein the trained unsupervised machine learning model is trained by simultaneously minimizing a first objective function using the training mixture spectra, and a second objective function using the synthetic water-cuts, the synthetic path-length fraction values, and the synthetic measured spectra.

20. The system of claim 12, wherein the synthetic water-cuts and the synthetic path-length fraction values are drawn from a uniform distribution, and the synthetic measured spectra are generated from the synthetic water-cuts and the synthetic path-length fraction values using a Beer-Lambert Law.

* * * * *